United States Patent [19]

Styczynski et al.

[11] Patent Number: 5,962,466
[45] Date of Patent: Oct. 5, 1999

[54] REDUCTION OF HAIR GROWTH USING INHIBITORS OF MATRIX METALLOPROTEINASES

[76] Inventors: Peter Styczynski, P.O. Box 387, Mount Airy, Md. 21771; Gurpreet S. Ahluwalia, 8632 Stableview Ct., Gaithersburg, Md. 20882; Douglas Shander, 16112 Howard Landing Dr., Gaithersburg, Md. 20878

[21] Appl. No.: 09/014,187
[22] Filed: Jan. 27, 1998

Related U.S. Application Data

[63] Continuation-in-part of application No. 08/764,980, Dec. 13, 1996, abandoned.
[51] Int. Cl.⁶ .................................................. A61K 31/44
[52] U.S. Cl. ........................ 514/292; 514/17; 514/19; 514/80; 514/119; 514/182; 514/247; 514/428; 514/438; 514/560; 514/626; 514/665; 514/152; 514/699
[58] Field of Search .................................... 514/292, 438, 514/626, 665, 560, 247, 428, 119, 19, 17, 80, 699, 182, 152

[56] References Cited

U.S. PATENT DOCUMENTS

| | | |
|---|---|---|
| 3,426,137 | 2/1969 | Philpitt et al. . |
| 4,039,669 | 8/1977 | Beyler et al. . |
| 4,139,638 | 2/1979 | Neri et al. . |
| 4,161,540 | 7/1979 | Neri et al. . |
| 4,191,775 | 3/1980 | Glea . |
| 4,269,831 | 5/1981 | Ferrari et al. . |
| 4,370,315 | 1/1983 | Greff et al. . |
| 4,439,432 | 3/1984 | Peat . |
| 4,508,714 | 4/1985 | Cecic et al. . |
| 4,517,175 | 5/1985 | Iwabuchi et al. . |
| 4,720,489 | 1/1988 | Shander . |
| 4,885,289 | 12/1989 | Brener et al. . |
| 4,935,231 | 6/1990 | Pigiet . |
| 5,095,007 | 3/1992 | Ahluwalia . |
| 5,096,911 | 3/1992 | Ahluwalia et al. . |
| 5,132,293 | 7/1992 | Shander et al. . |
| 5,143,925 | 9/1992 | Shander et al. . |
| 5,189,212 | 2/1993 | Ruenitz . |
| 5,271,942 | 12/1993 | Heverhagen . |
| 5,300,284 | 4/1994 | Wiechers et al. . |
| 5,364,885 | 11/1994 | Ahluwalia et al. . |
| 5,411,991 | 5/1995 | Shander et al. . |
| 5,455,234 | 10/1995 | Ahluwalia et al. . |
| 5,474,763 | 12/1995 | Shander et al. . |
| 5,554,608 | 9/1996 | Ahluwalia et al. . |

FOREIGN PATENT DOCUMENTS

| | | |
|---|---|---|
| 0 309 086 | 3/1989 | European Pat. Off. . |
| 0413528A1 | 10/1990 | European Pat. Off. . |
| 0532219A2 | 2/1992 | European Pat. Off. . |
| 1 458 349 | 12/1976 | United Kingdom . |
| WO 95/24921 | 9/1995 | WIPO . |
| WO 98/02134 | 1/1998 | WIPO . |

OTHER PUBLICATIONS

Liu et al., Elsevier Science Ireland Ltd, Supression of type IV collagenase in MDA–MB–435 human breast cancer cells by eicosapentaenoic acid in vitro and in vivo, 21–26, 1995.

Tanaka et al., Cancer Research, Cyclic AMP–regulated Synthesis of the Tissue Inhibitors of Metalloproteinases Suppresses the Invasive Potential of the Human Fibrocarsoma Cell Line HT1080, 2927–35, 1995.

Inoue et al., The Society For Investigative Dermatology, Inc., Collagenase Expression Is Rapidly Induced in Wound–Edge Keratinocytes After Acute Injury in Human Skin, . . . 479–83, 1995.

Davies et al., Arthritis & Rheumatism, Inhibition of Collagenase Activity by N–Chlorotaurine, a Product of Activated Neutrophils, 424–27, 1994.

Bird et al., Journal of Medical Chemistry, Synthesis of Novel N–Phosphonoalkyl Dipeptide Inhibitors of Human Collagenase, 158–69, 1994.

Kleiner et al., Analytical Biochemistry, Quantitative Zymography: Detection of Picogram Quantities of Gelatinases, 325–29, 1994.

Lafuma et al., The Journal of Investigative Dermatology, Expression of 72–kDa Gelatinase (MMP–2), Collagenase (MMP–1), and Tissue Metalloproteinase Inhibitor (TIMP) in Primary Pig Skin . . . , 945–50, 1994.

Mauch et al., Arch. Dermatol. Res., "Role of the extracellular matrix in the degradation of connective tissue", 107–14, 1994.

Harmon et al., British Journal of Dermatology, "Hair Fibre Production by Human Hair Follicle in Whole–organ Culture", 415–423, 1994.

Harmon et al., Sid Abstracts, "12–O–Tetradecanoylphorbol–12–Acetate Inhibits Human Hair Follicles Growth and Hair Fiber Production in Whole–organ Cultures," 102:533 1994.

Philpott et al., Journal of Dermatological Science, "Human Hair Growth in vitro: A Model for the Study of Hair Follicle Biology," 7:s55–s72, 1994.

Jindo et al., The Journal of Dermatology, "Organ Culture of Mouse Vibrissal Hair Follicles in Serum–free Medium," 20:756–762, 1993.

Messenger, The Society For Investigative Dermatology, "The Control of Hair Growth: An Overview," 1011:4s–9s, 1993.

Li et al., Proc. Natl. Acad. Sci. USA, "Hair Shaft Elongation, Follicle Growth, and Spontaneous Regression in Long–term, Gelatin Sponge–supported Histoculture of Human Scalp Skin," 89:8764–8768, 1992.

Li et al., In vitro Cell. Dev. Biol., "Skin Histoculture Assay for Studying the Hair Cycle," 28A:695–698, 1992.

Grobelny et la., Biochemistry, "Inhibition of Human Skin Fibroblast Collagenase, Thermolysin, and Pseudomona aeruginosa elastase by Peptide Hydroamic Acids", 7152–54, 1992.

Woessner, The FASEB Journal, Matrix metalloproteinases and their inhibitors in connective tissue remodeling 2145–54, 1991.

(List continued on next page.)

*Primary Examiner*—Rebecca Cook
*Attorney, Agent, or Firm*—Fish & Richardson P.C.

[57] ABSTRACT

Mammalian hair growth is reduced by inhibiting the activity of a matrix metalloproteinase in the skin.

35 Claims, No Drawings

OTHER PUBLICATIONS

Salzer et al., Pharmacology Hear. Res., "Cochlear Damage and Increased Threshold in Alpha–difluoromethylornithine DFMO Treated Guinea Pigs," 451–2:101–112, 1990 Abstract.

Emonard, Cellular and Molecular Biology, "Matrix Metalloproteinases. A Review.", 131–53, 1990.

Wang et al., Cancer Research, "Blocking of Collagenase Secretion by Estramustine during in Vitro Tumor Cell Invasion", 6262–71, 1988.

Umezawa et al., The Journal of Antibiotics, "Production of Actinonin, An Inhibitor of Aminopeptidase M., By Actinomycetes", 1629–30, 1985.

Goos et al., Arch. Dermatol. Res., "An Improved Method for Evaluating Antiandrogens," 273:333–341, 1982.

Zucker et al., JNCI, "Diversity of Melanoma Plasma Membrane Proteinase: Inhibition of Collagenolytic and Cytolytic Activities by Minocycline", 517–25, 1985.

Johnson et al., Biochemistry, "Inhibition of Hexokinase and Protein Kinase Activities of Tumor Cells by a Chloromethyl Ketone Derivative of Lactic Acid," 2112:2984–2989, 1982.

Simpson et al., British Journal of Dermatology, "The Effect of Topically Applied Progesterone on Sebum Excretion Rate," 100:687–692, 1979.

Sato, Biology and Disease of the Hair, "The Hair Cycle and its Control Mechanism," 3–13, 1976.

Adachi et al., J. Soc. Cosmet. Chem., "Human Hair Follicles: Metabolism and Control Mechanisms," 21:901–924, 1970.

Kawabe, J. Cell. Biol., 111 (5 parts), p. 15a, 1990.

Horrobin et al., CA 111:159983, 1989.

WPIDS, AN97–042830, Dec. 12, 1996.

REDUCTION OF HAIR GROWTH USING INHIBITORS OF MATRIX METALLOPROTEINASES

This is a continuation-in-part of U.S. application Ser. No. 08/764,980, filed Dec. 13, 1996, abandoned.

The invention relates to reducing hair growth in mammals.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic antiandrogens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gammaglutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; Shander et al., U.S. Pat. No. 5,132,293; and Shander et al., U.S. Pat. No. 5,143,925.

Matrix metalloproteinases (MMPs) are a family of proteolytic enzymes which together, are capable of breaking down specific protein components of the extracellular matrix, including collagen, laminin and fibronectin. At least 9 different matrix metalloproteinases have been identified, including MMP-1 (interstitial collagenase), MMP-2 (72 kD collagenase), MMP-3 (stromelysin), MMP-4 (telopeptidase), MMP-5 (collagen endopeptidase), MMP-6 (acid metalloproteinase), MMP-7 (uterine metalloproteinase), MMP-8 (neutrophil collagenase), and MMP-9 (92 kD collagenase).

Several common characteristics are shared by members of the MMP family. For example, their catalytic activity is dependent upon zinc at the active center; their secreted form can be activated by other proteinases; their cDNA sequences all show homology; they can act upon one or more components of the extracellular matrix, often with overlapping substrate specificity; and their activity can be regulated, at least in part, by endogenous inhibitors. See generally Emonard and Grimaud, Cell. Molec. Biol. 36:131–53, (1990); Mauch et al., Arch. Dermatol. Res. 287: 107–14, (1994).

MMPs are present in all tissues including skin and hair follicles, although their role in these two tissues remains obscure. In general, these enzymes play a significant role in physiological processes such as re-epithelialization that occurs during wound healing. Additionally, MMPs may contribute to the pathogenesis of a variety of disease states. It also is possible that MMPs contribute to the extensive cell migration during continuous renewal that both skin and hair follicles undergo (Lafuma et al., J. Invest. Dermatol. 102: 945–950, 1994; Inoue et al. J. Invest. Dermatol. 104: 479–483, 1995).

Both direct and indirect inhibitors of MMPs are known. One form of indirect inhibition of MMPs involves stimulating an increase in the expression or catalytic activity of endogenous tissue-derived inhibitors of MMP. Known indirect inhibitors that apparently act via this mechanism include bromo-cyclic adenosine monophosphate; protocatechuic aldehyde (3,4-dihydroxybenzaldehyde); and estramustine (estradiol-3-bis(2-chloroethyl)carbamate).

It has now been found that unwanted mammalian (including human) hair growth—particularly androgen-stimulated hair growth—can be reduced by applying to the skin a composition including an inhibitor of an MMP in an amount effective to reduce hair growth. The unwanted hair growth which is reduced may be normal hair growth, or hair growth that results from an abnormal or diseased condition.

Examples of inhibitors of an MMP include 1,10-phenanthroline (o-phenanthroline); batimastat also known as BB-94; [4-(N-hydroxyamino)-2R-isobutyl-3S-(thiopen-2-ylthiomethyl)-succinyl]-L-phenylalanine-N-methylamidecarboxyalkylamino-based compounds such as N-[1-(R)-carboxy-3-(1,3-dihydro-2H-benz[f]isoindol-2-yl)propyl]-N',N'-dimethyl-L-leucinamide, trifluoroacetate (J. Med Chem. 36:4030–4039, 1993); marimastat (BB-2516); N-chlorotaurine; eicosapentaenoic acid; matlystatin-B; actinonin (3-[[1-[[2-(hydroxymethyl)-1-pyrolidinyl]carbamoyl]-octanohydroxamic acid); N-phosphonalkyl dipeptides such as N-[N-((R)-1-phosphonopropyl)-(S)-leucyl]-(S)-phenylalanine-N-methylamide (J. Med. Chem. 37:158–169, 1994); peptidyl hydroxamic acids such as pNH$_2$-Bz-Gly-Pro-D-Leu-D-Ala-NHOH (Biophys. Biochem. Res. Comm. 199: 1442–1446, 1994); Ro-31-7467, also known as 2-[(5-bromo-2,3-dihydro-6-hydroxy-1,3-dioxo-1Hbenz[de]isoquinolin-2-yl)methyl](hydroxy)-[phosphinyl]-N-(2-oxo-3-azacyclotridecanyl)-4-methylvaleramide; CT1166, also known as N1{N-[2-(morpholinosulphonylamino)-ethyl]-3-cyclohexyl-2-(S)-propanamidyl}-N4-hydroxy-2-(R)-[3-(4-methylphenyl)propyl]-succinamide (Biochem. J. 308:167–175, 1995); bromocyclic-adenosine monophosphate; protocatechuic aldehyde (3,4-dihydroxybenzaldehyde); estramustine (estradiol-3-bis(2-chloroethyl)carbamate); tetracycline (4-(dimethylamino)-1,4,4a,5,5a,6,11,12a-octahydro-3,6,10,12,12a-pentahydroxy-6-methyl-1,11-dioxo-2-naphthacenecarboxamide); minocycline (7-dimethylamino-6-dimethyl-6-deoxytetracycline); methacycline (6-methylene oxytetracycline); and doxycycline (α-6-deoxy-5-hydroxytetracycline). Preferably, the inhibitor of an MMP includes an inhibitor other than an unsaturated fatty acid such as eicosapentaenoic acid.

A particular inhibitor may inhibit more than one MMP. The inhibitor may inhibit, for example, MMP-1 (interstitial collagenase), MMP-2 (72 kD collagenase), MMP-3 (stromelysin), MMP-4 (telopeptidase), MMP-5 (collagen endopeptidase), MMP-6 (acid metalloproteinase), MMP-7 (uterine metalloproteinase), MMP-8 (neutrophil collagenase), and/or MMP-9 (92 kD collagenase). Direct and/or indirect inhibitor of an MMP may be used.

The inhibitors of the MMP preferably are incorporated in a topical composition that preferably includes a non-toxic dermatologically acceptable vehicle or carrier which is adapted to be spread upon the skin. Examples of suitable vehicles are acetone, alcohols, or a cream, lotion, or gel which can effectively deliver the active compound. One such vehicle is disclosed in co-pending application PCT/US93/0506A. In addition, a penetration enhancer may be added to the vehicle to further enhance the effectiveness of the formulation.

The concentration of the inhibitor in the composition may be varied over a wide range up to a saturated solution, preferably from 0.1% to 30% by weight or even more; the reduction of hair growth increases as the amount of inhibitor applied increases per unit area of skin. The maximum amount effectively applied is limited only by the rate at which the inhibitor penetrates the skin. The effective amounts may range, for example, from 10 to 3000 micrograms or more per square centimeter of skin.

The composition should be topically applied to a selected area of the body from which it is desired to reduce hair growth. For example, the composition can be applied to the face, particularly to the beard area of the face, i.e., the cheek, neck, upper lip, and chin. The composition can also be applied to the legs, arms, torso or armpits. The composition is particularly suitable for reducing the growth of unwanted hair in women suffering from hirsutism or other conditions. In humans, the composition should be applied once or twice a day, or even more frequently, for at least three months to achieve a perceived reduction in hair growth. Reduction in hair growth is demonstrated when the frequency or hair removal is reduced, or the subject perceives less hair on the treated site, or quantitatively, when the weight of hair removed by shaving (i.e., hair mass) is reduced.

Male intact Golden Syrian hamsters are considered acceptable models for human beard hair growth in that they display oval shaped flank organs, one on each side, each about 8 mm. in major diameter, which grow thick black and coarse hair similar to human beard hair. These organs produce hair in response to androgens in the hamster. To evaluate the effectiveness of a composition including an inhibitor of an MMP, the flank organs of each of a group of hamsters are depilated by applying a thioglycolate based chemical depilatory (Surgex). To one organ of each animal 10 $\mu$l. of vehicle alone once a day is applied, while to the other organ of each animal an equal amount of vehicle containing an inhibitor of a matrix metalloproteinase is applied. After thirteen applications (one application per day for five days a week), the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

The above-described assay will be referred to herein as the "Golden Syrian hamster" assay. Preferred compositions provide a reduction in hair growth of at least about 25%, more preferably at least about 50%, and most preferably at least about 60% when tested in the Golden Syrian hamster assay. A number of inhibitors were tested in the Golden Syrian hamster assay; the results are provided in Table 1:

TABLE I

Effect of Matrix Metalloproteinase Inhibitors on Hair Mass

| | | | | | Hair Mass (mg) | |
|---|---|---|---|---|---|---|
| Compound | Vehicle | pH | Dose | % Reduction | Treated | Vehicle Control |
| Br-cAMP | A | 4.5 | 10% | 80 ± 6 | 0.42 ± .12 | 2.00 ± .20 |
| Minocycline | A | 4.0 | 10% | 63 ± 6 | 0.82 ± .11 | 2.27 ± .15 |
| Methacycline | A | 4.0 | 10% | 57 ± 9 | 0.68 ± .11 | 1.75 ± .25 |
| Tetracycline | B | 4.5 | 10% | 56 ± 9 | 0.67 ± .10 | 1.61 ± .14 |
| 1,10-Phenanthroline | A | 7.0 | 5% | 45 ± 9 | 1.40 ± .24 | 2.51 ± .25 |
| Protocatechuic aldehyde | A | 3.5 | 10% | 32 ± 9 | 0.92 ± .13 | 1.40 ± .23 |
| Doxycycline | A | 5.5 | 10% | 27 ± 9 | 1.73 ± .22 | 2.44 ± .21 |

Vehicle A: 68% $H_2O$; 16% ethanol; 5% propylene glycol; 5% dipropylene glycol; 4% benzyl alcohol; 2% propylene carbonate.
Vehicle B: 50% dimethylsulfoxide; 40% ethanol; 8.75% $H_2O$; 1% propylene glycol dipelargonate; 0.25% propylene glycol.

The matrix metalloproteinases MMP-2 (72 kD collagenase) and MMP-9 (92 kD collagenase) were assayed in flank organ hair follicle homogenates using a zymographic assay. Zymography is an electrophoretic technique used to identify proteolytic activity in enzymes separated in polyacrylamide gels under nondenaturing conditions (Kleiner and Stetler-Stevenson, Analytical Biochemistry 218: 325–329, 1994). Flank organ hair follicles were removed from untreated hamsters and homogenized in a buffer containing 25 mM Tris, pH 7.5, and 50 mM sucrose. Samples of the homogenate were added to an equal volume of zymogram sample buffer containing 63 mM Tris-HCl, pH 6.8, 10% glycerol, 2% SDS, and 0.0025% bromophenol blue. (Note: all buffers and acrylamide gels were obtained from Novex, San Diego, Calif.). The samples were incubated for 10 minutes at room temperature and then loaded onto a precast 10% Tris-Glycine gel with 0.1% gelatin incorporated throughout the gel. The gel was electrophoresed at 125 constant volts for about 90 minutes. The gel was incubated for 30 minutes in renaturing buffer consisting of 2.5% triton X-100 followed by incubation in developing buffer which contained 10 mM Tris-base, 40 mM Tris-HCl, 200 mM NaCl, 5 mM $CaCl_2$, and 0.02% Brij 35. The developing buffer was decanted after 30 minutes and replaced with fresh buffer for incubation overnight.

For inhibition experiments, the inhibitor was included in the renaturing and development buffer steps. The gel was stained with Coomassie blue 0.25% for 1 hour and then destained overnight. Transparent bands were visualized against a blue background. MMP-2 and MMP-9 standards were supplied by Oncologix (Gaithersburg, Md.). The relative degree of digestion, representing collagenase activity, was quantitated by scanning photographs of the gels using Adobe Photoshop (Adobe Systems Inc., Mountain View, Calif.) and IPLab Gel (Signal Analytics, Vienna, Va.) software. The images were digitally inverted so that the integrations of bands would be reported as positive values. This method of analysis was standardized with respect to protein concentration. The results are provided in Table 2 and Table 3.

TABLE II

Percent Inhibition of Flank Organ MMP-2 Collagenase Activity

| Compound | Concentration | | |
|---|---|---|---|
| | 0.1 mM | 0.5 mM | 1 mM |
| Tetracycline | 31 | 64 | 100 |
| Minocycline | — | — | 100 |
| Doxycycline | 89 | 100 | — |
| Methacycline | — | — | 100 |
| 1,10-Phenanthroline | 100 | 100 | — |

— = concentrations were not tested.

TABLE III

Percent Inhibition of Flank Organ MMP-9 Collagenase Activity

| Compound | Concentration | | |
|---|---|---|---|
| | 0.1 mM | 0.5 mM | 1 mM |
| Tetracycline | 49 | 70 | 100 |
| Minocycline | — | — | 100 |
| Doxycycline | 28 | 100 | — |
| Methacycline | — | — | 100 |
| 1,10-Phenanthroline | 100 | 100 | — |

— = concentrations were not tested.

Other embodiments are within the claims.

We claim:

1. A method of reducing mammalian hair growth which comprises
   selecting an area of skin from which reduced hair growth is desired; and
   applying to said area of skin a dermatologically acceptable composition comprising an inhibitor of a matrix metalloproteinase other than an unsaturated fatty acid in an amount effective to reduce hair growth.

2. The method of claim 1, wherein said inhibitor is 1,10-phenanthroline.

3. The method of claim 1, wherein said inhibitor is batimastat.

4. The method of claim 1, wherein said inhibitor is marimastat.

5. The method of claim 1, wherein said inhibitor is N-chlorotaurine.

6. The method of claim 1, wherein said inhibitor is matlystatin-B.

7. The method of claim 1, wherein said inhibitor is actinonin.

8. The method of claim 1, wherein said inhibitor is an N-phosphonalkyl dipeptide.

9. The method of claim 8, wherein said inhibitor is N-[N-((R)-1-phosphonopropyl)-(S)-leucyl]-(S)-phenylalanine-N-methylamide.

10. The method of claim 1, wherein said inhibitor is peptidyl hydroxamic acid.

11. The method of claim 10, wherein said inhibitor is pNH$_2$-Bz-Gly-Pro-D-Leu-D-Ala-NHOH.

12. The method of claim 1, wherein said inhibitor is 2-[(5-bromo-2,3-dihydro-6-hydroxy-1,3-dioxo-1Hbenz[de]isoquinolin-2-yl)methyl](hydroxy)-[phosphinyl]-N-(2-oxo-3-azacyclotridecanyl)-4-methylvaleramide.

13. The method of claim 1, wherein said inhibitor is an analogue of N1{N-[2-(morpholinosulphonylamino)-ethyl]-3-cyclohexyl-2-(S)-propanamidyl}-N4-hydroxy-2-(R)-[3-(4-methylphenyl)propyl]-succinamide.

14. The method of claim 1, wherein said inhibitor is bromo-cyclic adenosine monophosphate.

15. The method of claim 1, wherein said inhibitor is protocatechuic aldehyde.

16. The method of claim 1, wherein said inhibitor is estramustine.

17. The method of claim 1, wherein said inhibitor is 4-(dimethylamino)-1,4,4a,5,5a,6,11,12a-octahydro-3,6,10,12,12a-pentahydroxy-6-methyl-1,11-dioxo-2-naphthacenecarboxamide.

18. The method of claim 1, wherein said inhibitor is 7-dimethylamino-6-dimethyl-6-deoxytetracycline.

19. The method of claim 1, wherein said inhibitor is 6-methylene oxytetracycline.

20. The method of claim 1, wherein said inhibitor is α-6-deoxy-5-hydroxytetracycline.

21. The method of claim 1, wherein the concentration of said inhibitor of in said composition is between 0.1% and 30%.

22. The method of claim 1, wherein the composition provides a reduction in hair growth of at least 25% when tested in the Golden Syrian hamster assay.

23. The method of claim 1, wherein the composition provides a reduction in hair growth of at least 50% when tested in the Golden Syrian hamster assay.

24. The method of claim 1, wherein the composition provides a reduction in hair growth of at least 60% when tested in the Golden Syrian hamster assay.

25. The method of claim 1, wherein the inhibitor is applied to the skin in an amount of from 10 to 3000 micrograms of said inhibitor per square centimeter of skin.

26. The method of claim 1, wherein said mammal is a human.

27. The method of claim 25, wherein said area of skin is on the face of the human.

28. The method of claim 25, wherein said area of skin is on a leg of the human.

29. The method of claim 25, wherein said area of skin is on an arm of the human.

30. The method of claim 25, wherein said area of skin is in an armpit of the human.

31. The method of claim 25, wherein said area of skin in on the torso of the human.

32. The method of claim 25, wherein said human is a woman suffering from hirsutism.

33. A method of reducing mammalian hair growth which comprises
    selecting an area of skin from which reduced hair growth is desired; and
    applying to said area of skin a dermatologically acceptable composition comprising an inhibitor of matrix metalloproteinase-2 other than an unsaturated fatty acid in an amount effective to reduce hair growth.

34. A method of reducing mammalian hair growth which comprises
    selecting an area of skin from which reduced hair growth is desired; and
    applying to said area of skin a dermatologically acceptable composition comprising an inhibitor of matrix metalloproteinase-9 other than an unsaturated fatty acid in an amount effective to reduce hair growth.

35. A method of reducing mammalian hair growth which comprises
    selecting an area of skin from which reduced hair growth is desired; and
    applying to said area of skin a dermatologically acceptable composition comprising a compound that increases the activity of an endogenous tissue-derived inhibitor of a matrix metalloproteinase other than an unsaturated fatty acid in an amount effective to reduce hair growth.

* * * * *